United States Patent
Katoh et al.

(10) Patent No.: US 8,551,073 B2
(45) Date of Patent: Oct. 8, 2013

(54) CATHETER DEVICE

(75) Inventors: Osamu Katoh, Aichi (JP); Shinji Ozawa, Aichi-ken (JP); Tomihisa Kato, Aichi-ken (JP)

(73) Assignees: Osamu Katoh, Kyoto-fu (JP); Asahi Intecc Co., Ltd., Aichi-ken (JP)

(*) Notice: Subject to any disclaimer, the term of this patent is extended or adjusted under 35 U.S.C. 154(b) by 809 days.

(21) Appl. No.: 12/457,379

(22) Filed: Jun. 9, 2009

(65) Prior Publication Data

US 2009/0254107 A1 Oct. 8, 2009

Related U.S. Application Data (62) Division of application No. 10/776,637, filed on Feb. 12, 2004, now abandoned.

(30) Foreign Application Priority Data

Feb. 17, 2003 (JP) .................................. 2003-037550

(51) Int. Cl.
*A61M 25/00* (2006.01)

(52) U.S. Cl.
USPC ....................................................... 604/526

(58) Field of Classification Search
USPC ............. 604/164.03, 164.06, 164.09, 164.13, 604/173, 40, 523, 525, 534–536, 526; 623/1.11; 606/191, 192, 194
See application file for complete search history.

(56) References Cited

U.S. PATENT DOCUMENTS

| | | | |
|---|---|---|---|
| 3,028,720 A | 4/1962 | Houk | 57/25 |
| 4,516,972 A | 5/1985 | Samson | 604/526 |
| 5,007,896 A | 4/1991 | Shiber | 604/22 |
| 5,373,619 A * | 12/1994 | Fleischhacker et al. | 29/451 |
| 5,653,696 A * | 8/1997 | Shiber | 604/267 |
| 6,106,538 A | 8/2000 | Shiber | 606/184 |
| 6,168,571 B1 | 1/2001 | Solar et al. | 600/585 |
| 6,296,651 B1 | 10/2001 | Lary et al. | 606/170 |
| 6,342,066 B1 | 1/2002 | Toro et al. | 623/1.11 |
| 6,368,344 B1 | 4/2002 | Fitz | 623/1.11 |
| 6,482,217 B1 | 11/2002 | Pintor et al. | 606/159 |
| 6,589,227 B2 | 7/2003 | Sønderskov Klint | 604/524 |
| 7,323,001 B2 * | 1/2008 | Clubb et al. | 606/200 |
| 2001/0044633 A1 | 11/2001 | Klint | 606/200 |
| 2002/0151823 A1 | 10/2002 | Miyata et al. | 600/585 |

FOREIGN PATENT DOCUMENTS

| | | |
|---|---|---|
| EP | 1 243 283 | 9/2005 |
| JP | 01-131653 | 5/1989 |
| JP | 04-058961 | 2/1992 |
| JP | 09-056822 | 3/1997 |
| JP | 10-211205 | 8/1998 |

(Continued)

*Primary Examiner* — Kevin C Sirmons
*Assistant Examiner* — Deanna K Hall
(74) *Attorney, Agent, or Firm* — Morgan, Lewis & Bockius LLP (57) ABSTRACT

A catheter device (K, K1, K2 and K3) has a flexible hollow tube body (1) formed by a plurality of austenitic stainless steel wires (2) cylindrically stranded to provide a hollow structure. An inner surface of the flexible hollow tube body (1) has a convex-concave structure represented by the stainless steel wires (2) to provide helical grooves (30). A leading distal end of the flexible hollow tube body (1) is formed into a knife-edge circle configuration to provide a knife-edge circle front (3), thus imparting a perforative capability to improve its quality and performance.

5 Claims, 6 Drawing Sheets (56) References Cited

FOREIGN PATENT DOCUMENTS

| JP | 2000-513235 | 10/2000 |
| JP | 2001-321446 | 11/2001 |
| JP | 2002-143318 | 5/2002 |
| JP | 2002-143320 | 5/2002 |
| JP | 2002-275774 | 9/2002 |
| JP | 2002-539901 | 11/2002 |
| WO | WO 99/23958 | 5/1999 |
| WO | WO 00/09195 | 2/2000 |
| WO | WO 00/57944 | 10/2000 |
| WO | WO 01/47436 | 7/2001 |

* cited by examiner

CATHETER DEVICE

This application is a Divisional of U.S. patent application Ser. No. 10/776,637, filed Feb. 12, 2004 now abandoned and claims the benefit of the Japanese Patent Application No. 2003-037550, filed Feb. 17, 2003, both of which are hereby incorporated by reference in their entirety.

BACKGROUND OF THE INVENTION

The invention relates to a catheter device, into which a flexible tube body is incorporated.

DESCRIPTION OF THE RELATED ART

As a general usage, a catheter is inserted into a tourtous blood vessel or a somatic cavity to be introduced into a diseased area. In this situation, the catheter is manipulated outside a patient's body by pushing, pulling and rotating a handling section of the catheter. During the manipulating process, the catheter advances its leading distal end toward the diseased area to provide a necessary treatment with the diseased area.

In order to insure a smooth insertion and treatment for the catheter, it is important to provide the catheter with a high linearity in free state, a pliable or flexible property through its entire length and a good restorability from a bending deformation.

It is also desirable that the catheter has a gradient property represented by a high flexibility at the leading distal end and a reasonable rigidity at a rear portion. At the same time, a high torque transmissibility and good steerability are required for the catheter as mechanical properties so that the leading distal end can precisely respond to manipulating action of the handling section.

Prior references have been introduced as having a flexible tube for medical tool which can cope with the above mechanical properties. The prior references are Laid-open Japanese Patent Application No. 2002-275774 and International Japanese Publication No. 2000-513235 in which a group of metallic wires circular in cross section are cylindrically stranded to form a flexible tube structure.

When the prior references are used as a catheter and medical guide wire, they have technological advantages to reduce a weight per unit length based on a hollow tube structure, a high flexibility and good torque transmissibility brought by a wire-stranded body in which a group of metallic wires are stranded into a hollow structure.

However, both the prior references leave rooms for improvements in quality and performance because they are insufficient in terms of drilling (perforative) ability against a hard clot area (e.g., fibrous cap), stent-retaining ability and insertion-slidability into the blood vessel upon treating an obstruction area of the blood vessel.

Therefore, the present invention has been made with the above drawbacks in mind, it is a main object of the invention to provide a catheter device of high quality, into which a flexible hollow tube body is incorporated.

SUMMARY OF THE INVENTION

According to the present invention, there is provided a catheter device having a flexible hollow tube body in which a plurality of austenitic stainless steel wires are cylindrically stranded. An inner surface of the flexible hollow tube body has a convex-concave structure represented by the austenitic stainless steel wires to provide helical grooves. A leading distal end of the flexible hollow tube body is formed into a knife-edge circle configuration to provide a knife-edge circle front.

A catheter device is provided which uses a mono-layered tube in which the flexible hollow tube body is employed at least partly as a main tube.

According to other aspect of the present invention, there is provided a catheter in which a two-layered tube structure is formed by slidably fitting an upper-layered tube onto a lower-layered tube of a main tube body, and the upper-layered tube and the lower-layered tube are used as the flexible hollow tube body.

Alternatively, a three-layered structure is formed by slidably fitting the upper-layered tube onto the lower-layered tube with an outer tube slidably fit onto the upper-layered tube.

Due to the former aspect of the invention, a drilling (perforative) ability is imparted to a distal end of the flexible hollow tube body, while rendering an outer surface of the flexible hollow tube body highly smooth. This improves a performance of the catheter device when inserting the catheter device into the blood vessel and the somatic cavity for the purpose of therapeutically providing an appropriate treatment.

With the latter aspect of the invention, the catheter device is formed by two- or three-layered tube body. The catheter device has the multi-layered tube body in which stranding directions of the stainless steel wires are opposite among each layer of the tube bodies.

With the catheter device formed by the flexible hollow tube body, the catheter device is rotated, so that the knife-edge circular front advances to serve as a drill in order to perforate or push a hard clot area open when the guide wire introduces the catheter device, and confronts the hard clot area of a completely obstructed region in the blood vessel. This helps smoothly advance the catheter device into a true lumen so as to facilitate the proper treatment against the diseased area.

Further, a smooth outer surface of the flexible hollow tube body improves an insertion-slidability against the blood vessel and the somatic cavity so as to produce a catheter device of higher quality.

BRIEF DESCRIPTION OF THE DRAWINGS

A preferred form of the present invention is illustrated in the accompanying drawings in which.

DETAILED DESCRIPTION OF THE PREFERRED EMBODIMENTS

Figure 1:
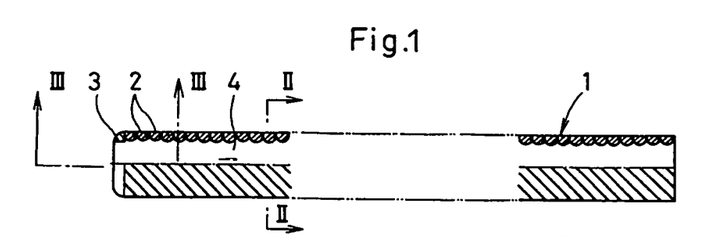
FIG. 1 is a plan view of a flexible hollow tube body of a catheter device according to a first embodiment of the invention but partly sectioned.
Figure 2:
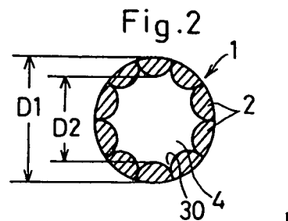
FIG. 2 is an enlarged latitudinal cross sectional view of the flexible hollow tube body taken along the line II-II of FIG. 1.
Figure 3:
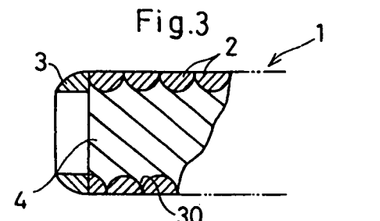
FIG. 3 is an enlarged longitudinal cross sectional view of a front portion of the flexible hollow tube body taken along the line III-III of FIG. 1.

Referring to FIGS. 1 through 3, a flexible hollow tube body 1 for a catheter device is shown according to a first embodiment of the invention. The flexible hollow tube body 1 (referred simply to as "tube body" hereinafter) is formed by cylindrically stranding a group of austenitic stainless steel wires 2 along a predetermined circle line to provide a flexible tube which has a certain length (L).

An inner surface of the tube body 1 forms a convex-concave structure represented by the stainless steel wires 2 generally formed semi-circular in cross section. An outer surface of the tube body 1 is rendered smooth consecutively in the lengthwise direction while the inner surface forms a hollow space 4 in which the convex-concave structure resides. A leading distal end of the tube body 1 is formed into a knife-edge circle configuration to provide a knife-edge circle front 3. The knife-edge circle front 3 is outwardly arcuated in cross section, and diametrically decreases progressively as approaching outward.

The tube body 1 is made from the metallic wires 2, the number of which is counted from eight to twelve, and the tube body 1 approximately measures 0.61 mm in outer diameter (D1) and 0.45 mm in inner diameter (D2).

Figure 4:
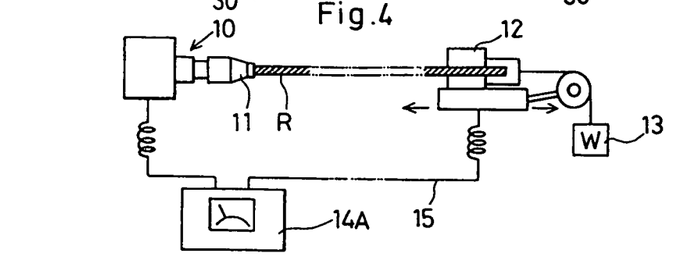
FIG. 4 is an explanatory view showing how the flexible hollow tube body is formed.

The tube body 1 is formed in a fashion as shown in FIG. 4. Namely, a wire rope R is provided by stranding the metallic wires 2 around an elongate core (not shown). One end of the wire rope R is secured to a rotational chuck 11 of a twisting device 10. The other end of the wire rope R is secured to a slidable chuck 12 from which a weight 13 is depended. The wire rope R is twisted under the tensile stress caused by the weight 13. A current generating device 14 supplies electric currents to the chucks 11 and 12 through an electric wire cord 15 so that the wire rope R is heated by its electric resistance to remove the residual stress appeared on the wire rope R during the twisting process.

Then, the outer surface of the tube body 1 is smoothly ground so that the metallic wires 2 forms semi-circular in cross section. The elongate core is withdrawn from the wire rope R to provide a hollow tube structure.

Figure 5:
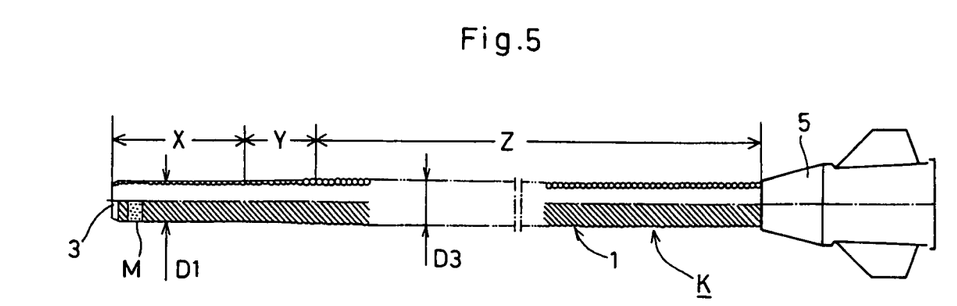
FIG. 5 is a plan view of a catheter device according to a second embodiment of the invention but partly sectioned.

FIG. 5 shows a catheter device K into which the tube body 1 is incorporated. The catheter device K has a flexible hollow tube body 1 as a main structure in which a plurality of the metallic wires 2 are stranded according to the method as depicted in FIG. 4. The tube body 1 has a front section in the lengthwise direction to serve as an X-zone in which the knife-edge circle front 3 situates on the leading distal end of the tube body 1.

A rear length portion of the catheter device K belongs to a Z-zone, and serves as a diameter-increased portion (denoted at D3 as its diameter) in which the metallic wires 2 form circular in cross section with its outer surface not ground.

A middle length portion of the catheter device K diametrically increases progressively from its front end (D1) to rear end (D3) to serve as a Y-zone between the front section and the rear length portion.

The structure is such that the catheter device K is flexible in the front portion and rigid in the rear portion as a necessary property given to the catheter device K. A connector 5 and a marker M are provided in a manner as is well known for those versed in the art. The knife-edge circle front 3 is provided by plasma welding a coil element of the metallic wire 2, and formed to be outwardly arcuated in cross section by means of grinder or the like. A circumferential surface of the knife-edge circle front 3 is rendered smooth.

By appropriately determining a distance between the plasma-welded top end and the marker M, it becomes possible to render a rigid-flexible degree of the leading end of the catheter device K adjustable.

Figure 6:
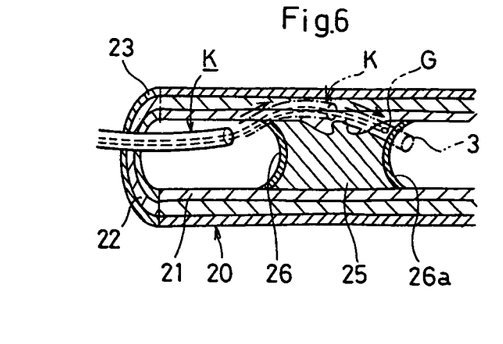
FIG. 6 is an explanatory view showing how the catheter device is manipulated.

Upon inserting the catheter device K against a completely obstructed area 25 in a blood vessel 20 to cure the obstructed area 25 as shown in FIG. 6, a guide wire G which introduces the catheter device K may meet a calcified hard clot area 26 (fibrous cap) of the completely obstructed area 25.

In this situation, the guide wire G is manipulated so that it detours the completely obstructed area 25 to be introduced between the media 22 and the adventitial coat 23 through the intima 21 of the blood vessel 20.

However, the guide wire G meets a hard clot area 26a again at the other side beyond the completely obstructed area 25 so as to hinder an advancement of the guide wire G.

In order to eliminate the hindrance, the catheter device K is advanced from the guide wire G, and rotated to use the knife-edge circle front 3 as a drill to perforate or push the hard clot area 26a open, thus helping the guide wire G smoothly advance into the true lumen. Hard clot powder pulverized by the knife-edge circle front 3 is carried away rearward along helical grooves 30 inside the tube body 1.

This enables the operator to eliminate an inconvenience caused by the fact that the pulverized hard clot powder remains inside.

The catheter device K is such that its rear end decreases diametrically as approaching the front end portion of the catheter device K. This amplifies the rotational force of the front end portion which undergoes the rotational torque from the handling section of the catheter device K. This insures a good drilling function of the knife-edge circle front 3 when the rear end of the catheter device K is rotated. The smooth outer surface of the front end portion (X-zone) of the catheter device K enables the operator to readily insert the catheter device K into the blood vessel and easily rotate the catheter device K within the blood vessel.

The group of the metallic wires 2 is twisted under the tensile stress along the lengthwise direction in accordance with the method as shown in FIG. 4. This gives the tube body 1 a high linearity property and a twist-deforming property. Each of the metallic wires 2 uniformly slides smoothly without variations to develop no gap between the helical line elements of the tube body 1, the gap of which often appears on an outer tensile side of a single-wound helical coil tube body when the tube body is bent in the blood vessel with a minimum diameter. This improves an insertability against the blood vessel, a rotation-following ability of the handling section and a torque transmissibility so as to insure a precise treatment with a high efficiency. The knife edge circle front 3 forms an outwardly tapered fashion and facilitates its insertion against the blood vessel.

Figures 7, 8:
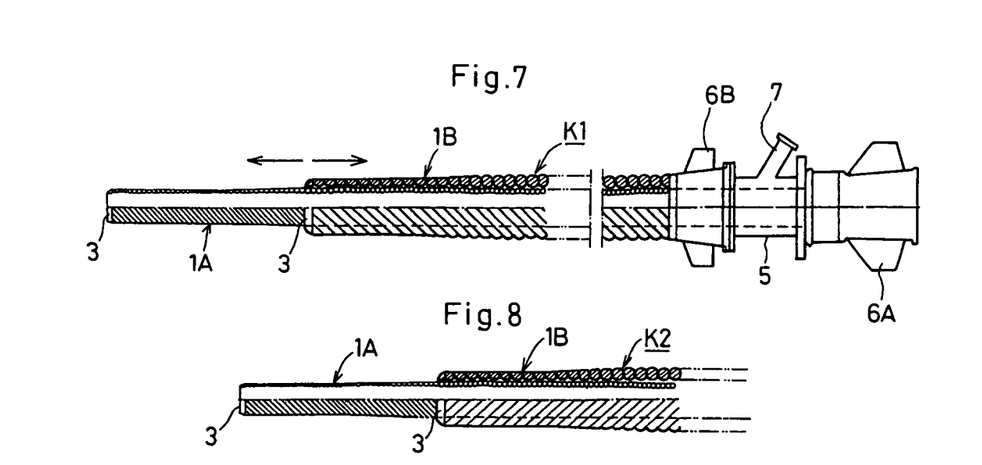
FIG. 7 is a plan view of a catheter device according to a third embodiment of the invention but partly sectioned.
FIG. 8 is a plan view of a front portion of a catheter device according to a fourth embodiment of the invention but partly sectioned.
Figure 9:
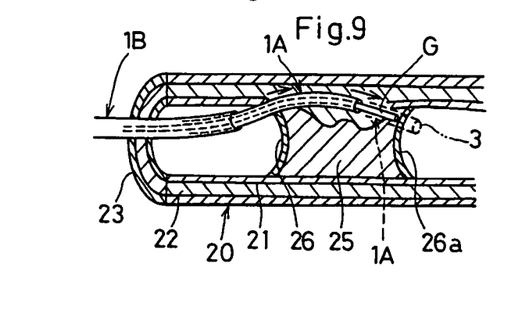
FIG. 9 is an explanatory view showing how the catheter device is manipulated.

FIGS. 7 through 9 show a third embodiment of the invention. In the third embodiment of the invention, a catheter device K1 has a lower-layered tube 1A provided as a main tube by the tube body 1 identical to that of the catheter device K in FIG. 5. An upper-layered tube 1B has the knife-edge circle front 3 at its leading distal end, and is diametrically increased to be slidably fit onto the catheter device K of FIG. 5.

FIG. 8 shows a catheter device K2 according to a fourth embodiment of the invention in which a stranding direction of the lower-layered tube 1A and that of the upper-layered tube 1B are mutually opposite by approximately 90 degrees (intersection angle between the lower metallic wires and the upper metallic wires).

For this reason, upon perforating the hard clot area 26a of the completely obstructed area 25 as shown in FIG. 9, the lower-layered tube 1A is manipulated first to provide a small hole on the hard clot area 26a, and then the upper-layered tube 1B is manipulated to advance from the lower-layered tube 1A to diametrically enlarge the small hole to a sufficient-sized hole, thus making it possible to easily perforate the hard clot area 26a.

In general, the vascular dilatation treatment has been implemented with the use of balloon catheters which are replaced in turn from diametrically smaller ones to diametrically larger ones. The replacing operation of the balloon catheters is done only by sliding the upper-layered tube 1B, thus facilitating the vascular dilatation treatment with a high efficiency.

The metallic wires 2 of the lower-layered tube 1A and that of the upper-layered tube 1B come to substantially engage in a point contact with the catheter device K2 in which the stranding direction of the lower-layered tube 1A and that of the upper-layered tube 1B are mutually opposite. This improves the slidability of the upper-layered tube 1B against the lower-layered tube 1A so as to render the upper-layered tube 1B easily manipulatable.

In the two-layered catheter device K2, a bending rigidity of the upper-layered tube 1B may be determined to be greater than that of the lower-layered tube 1A. A hydrophilic polymer (e.g., polyvinylpyrrolidone or the like) may be coated on sliding portions of the upper-layered tube 1B and the lower-layered tube 1A.

In the layered structure in which the bending rigidity of the upper-layered tube 1B is greater than that of the lower-layered tube 1A, a bending resistivity of the latter is positively held by the former. This prevents harmful deformations from being accumulated on the lower-layered tube 1A when the catheter device K2 is repeatedly bent with minimum diameters, whereby avoiding an insertion resistivity from being abnormally induced on the catheter device K2 when inserting the catheter device K2 into the blood vessel.

Figure 10:
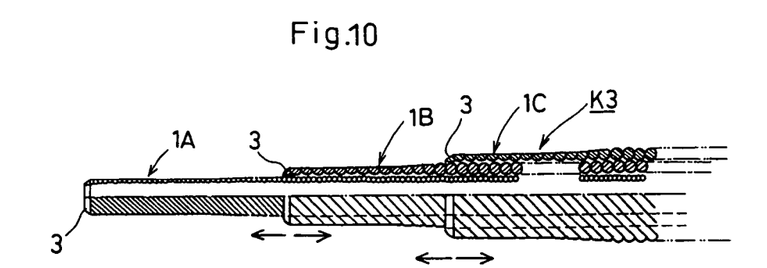
FIG. 10 is a plan view of a front portion of a catheter device according to a fifth embodiment of the invention.

FIG. 10 shows a fifth embodiment of the invention in which a catheter device K3 of multi-layered structure is provided.

In the fifth embodiment of the invention, an outer tube 1C is slidably fit onto the upper-layered tube 1B which is slidably fit onto the lower-layered tube 1A in the same manner as described at the third embodiment of the invention (referred to FIG. 7). The outer tube 1C is structurally identical to the upper-layered tube 1B to form a three-layered tube structure.

Figure 11:
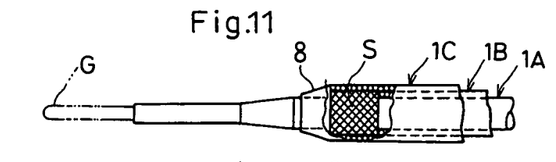
FIGS. 11 and 12 are explanatory views showing how a catheter device is manipulated according to a sixth embodiment of the invention.
Figure 12:
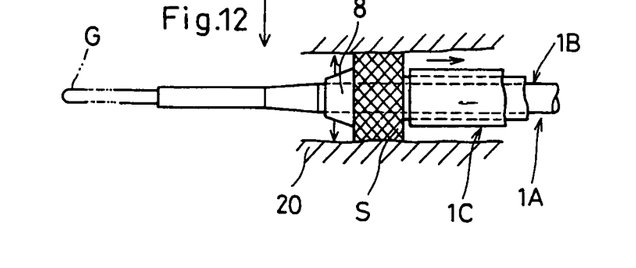

FIGS. 11 and 12 show a sixth embodiment of the invention in which a frustocone-shaped chip 8 is provided with the lower-layered tube 1A of the fifth embodiment of the invention. The chip 8 is formed by a metallic material (preferably radiopaque) or a synthetic resin. The chip 8 is diametrically decreases progressively as approaching forward. Between the chip 8 and a front section of the upper-layered tube 1B, a self-expansible stent S is provided. The stent S is pushed by the outer tube 1C to set it in position. Then, the stent S is placed in the diseased area of the blood vessel. The outer tube 1C slides rearward to let the stent S eject in itself so as to set it in the diseased area.

It is to be noted that the knife-edge circle front 3 of the upper-layered tube 1B may be omitted to improve the sliding performance between the lower-layered tube 1A, the upper-layered tube 1B and the outer tube 1C when the upper-layered tube 1B is made of a synthetic resin (e. g., polyethylene, fluoro-based plastics or the like).

The catheter device K3 of the three-layered tube structure enables an operator to readily retain the stent S on the diseased area of the blood vessel. This makes it possible for the operator to promptly treat the diseased area with a high efficiency, while reducing the time length period during which a subject patient suffers so as to significantly ameliorate the curability.

An inner surface of the outer tube 1C forms a concave-convex undulation which is consecutively in slidable contact with a zigzag coil line of the stent S. This makes the outer tube 1C come in a point contact with the stent S, thus enabling the operator to appropriately eject the stent S with a smooth operation upon pulling the outer tube 1C to release the stent S.

As an alternative usage of the catheter device K3, the lower-layered tube 1A is firstly used to provide a preliminary perforation, then the upper-layered tube 1B is used to provide a middle-sized perforation, and the outer tube 1C is finally used to complete a full-sized perforation against the hard clot area 26a (three-stage perforation). This makes it possible to insure a full-sized perforation with a precise manipulation.

Figure 13:
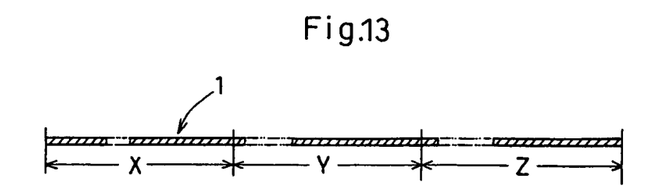
FIG. 13 is a plan view of a flexible hollow tube body according to a seventh embodiment of the invention.
Figure 14:
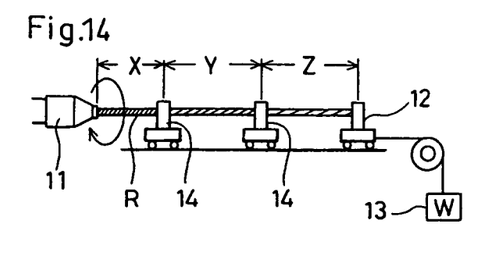
FIGS. 14 and 15 are explanatory views showing how the flexible hollow tube body is formed.
Figure 15:
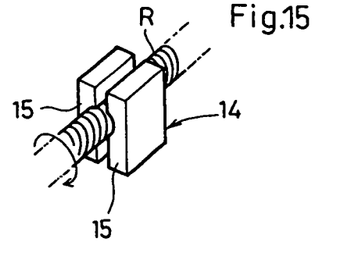

FIGS. 13 through 15 show a seventh embodiment of the invention which provides another method different from the first embodiment of the invention.

During the process of forming the tube body 1 (FIG. 4), the wire rope R is divided into the X-, Y- and Z-zones in the lengthwise direction. A clamp device 14 is mounted on the boundary portion between the X-, Y- and Z-zones, and has a pair of opposed clamp plates 15 which open and close to loosen and tighten the wire rope R as shown in FIGS. 14 and 15.

The wire rope R is twisted in different turns depending on the X-, Y- and Z-zones. This method renders the metallic wires 2 to be twisted in different turns so as to produce the tube body 1 as shown in FIG. 13. Among the mechanical properties needed for the catheter device, the tube body 1 has a bending property which corresponds in varying hardnesses to the X-, Y- and Z-zones depending on the numbers of twisting turns subjected. When the tube body 1 is used as a flexible linear wire for the catheter device, the most rigid section of the flexible linear wire corresponds to the handling section residing outside the subject patient.

The softer and more flexible section of the flexible linear wire corresponds to the leading end portion which is introduced into the blood vessel and the somatic cavity.

This produces the tube body 1 of high quality in which the bending rigidity changes to progressively increase or successively decrease in the lengthwise direction so as to provide a rigid-flexible gradient property.

Figure 16:
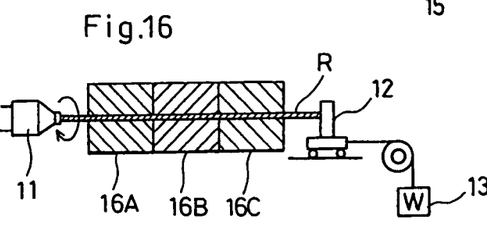
FIG. 16 is an explanatory view showing how a flexible hollow tube body is formed according to an eighth embodiment of the invention.

FIG. 16 shows an eighth embodiment of the invention in which heating devices 16A, 16B and 16C are provided. The wire rope R is set to the heating devices 16A, 16B and 16C in accordance with the lengthwise X-, Y- and Z-zones. During the process of twisting the wire rope R, or after taking the wire rope R out of the twisting device 10, the wire rope R is heat treated individually by the heating devices 16A, 16B and 16C. This makes it possible to produce the tube body 1 in which the residual stress is removed in varying degrees depending on the X-, Y- and Z-zones.

Depending on the different heating conditions of the heating devices 16A, 16B and 16C, the X-, Y- and Z-zones come to represent the residual stress removed in different degrees. For this reason, the tube body 1 functions as a highly effective catheter device in which the tensile strength and the bending rigidity gradually changes in the lengthwise direction so as to add good mechanical properties needed for the catheter device.

In the prior method of forming the flexible tube body, the tube body is provided by winding a metallic wire around a mandrel or using a winding machine (on paragraph [0004] of the Laid-open Japanese Patent Application No. 2002-275774 and on page 14 of the International Japanese Publication No. 2000-513235).

This develops a work hardening layer on one side of the metallic wire to often induce excessive gaps between the helical coil lines of the tube body when the tube body is bent to its minimum diameter, thus somewhat losing the rotational maneuverability and the torque transmissibility.

On the contrary, the method is such that the metallic wires 2 are twisted under the uniform tension to form the work hardening layer equally on an entire surface of the metallic wires 2. This makes the helical lines of the tube body 1 slide equally each other to avoid the excessive gaps from developing between the helical coil lines when the tube body 1 is bent to its minimum diameter, thus insuring a good rotational maneuverability and a torque transmissibility.

Figure 17:
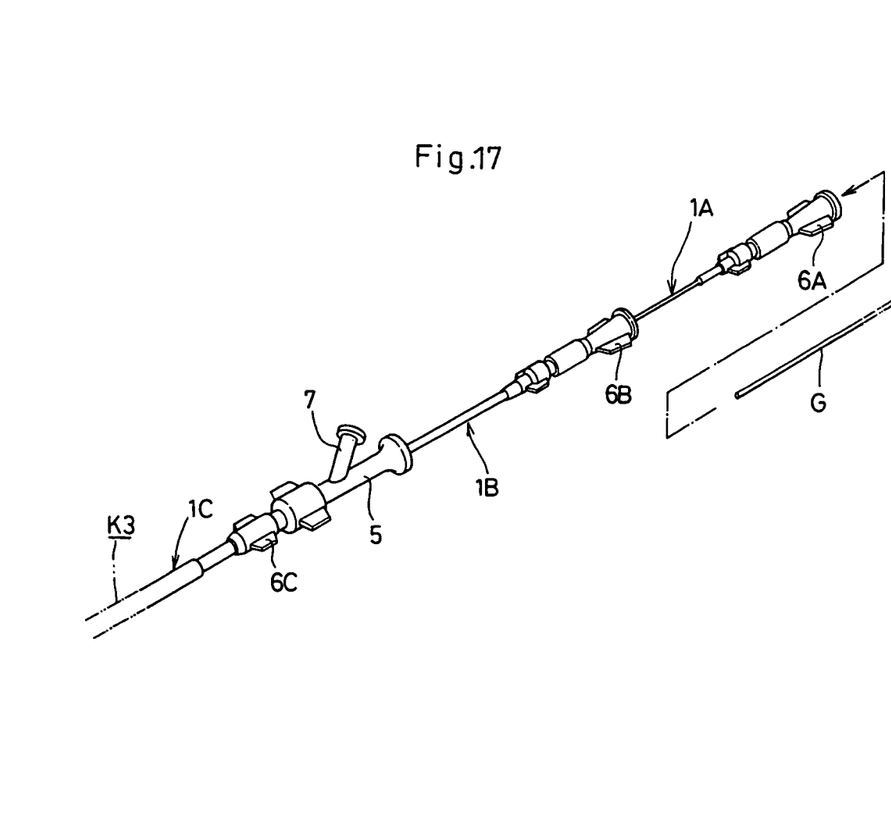
FIG. 17 is a view of a handling section of the catheter device.

FIG. 17 shows handling sections of the catheter device K3 in which the tube body 1 is of two- or three-layered structure (referred to FIG. 10). The catheter device K3 has the lower-layered tube 1A, the upper-layered tube 1B and the outer tube 1C, to which the manipulating portions 6A, 6B and 6C are respectively secured in a row. The manipulating portions 6A, 6B and 6C are individually pushed, pulled and rotated to enable the operator to perforate the hard clot area 26a and release the stent S.

The manipulating portions 6A, 6B and 6C may be formed differently from a wing-shaped one provided around respective boss portions. Between the manipulating portions 6B and 6C, a connector 5 is provided which has an injector 7 to introduce contrast media into the blood vessel. In the catheter device K1 of two-layered structure (referred to FIG. 7), only the manipulating portions 6A and 6B are provided in a row.

It is preferable to use the austenitic stainless steel for the present catheter. With the use of the austenitic stainless steel, its low thermal conductivity makes it possible to avoid the heat conduction from unnecessarily spreading upon welding the knife-edge circle front 3 and marker M, thus preventing the catheter device from deteriorating with a limited amount of electric currents and a reduced period of welding time.

As apparently from the foregoing description, the tube body for the catheter device enhances its performance and function, thus enabling the operator to perforate the hard clot area and to readily retain the stent in the diseased area so as to significantly improve the curability and the convenience of the subject patient.

It is to be noted that the knife-edge circle front 3 may be formed by welding a discrete a coil or ring line to a front tip coil end of the tube body 1, or the knife-edge circle front 3 may be integrally provided by press deforming the front tip coil end of the tube body 1.

Alternatively, the front tip coil end of the tube body 1 may be embedded in a plastic ring which serves as the knife-edge circle front 3.

What is claimed is:

1. A catheter device comprising:
   a flexible hollow tube body formed by a plurality of austenitic stainless steel wires tightly stranded cylindrically into a wire-rope configuration;
   a front end portion of an outer surface of said flexible hollow tube body being rendered smooth consecutively along a lengthwise direction of said flexible hollow tube body;
   a knife-edge circle front welded to a leading end of said flexible hollow tube body to serve as a blade which diametrically decreases progressively as approaching forward, a blade edge of said knife-edge circle front being outwardly arcuated in cross section from an entire outer surface of said knife-edge circle front along an axial direction thereof, and
   said knife-edge circle front being advanced to be rotated as a drill from a guide wire so as to perforate a hard clot area of an obstructed area, said hard clot area being pulverized by said knife-edge circle front to produce a hard clot powder; and
   helical grooves provided at an inner surface of said flexible hollow tube body, said helical grooves being formed by said austenitic stainless steel wires helically and tightly stranded in abutting relationship with each other,
   so as to carry away said hard clot powder in a rearward direction therealong.

2. The catheter device according to claim 1, wherein a two-layered structure is formed by slidably fitting an upper-layered tube onto a lower-layered tube of a main tube body,
   said upper-layered tube and said lower-layered tube each being made of said flexible hollow tube body, in which a stranding direction of said stainless steel wires of said lower-layered tube and that of said upper-layered tube are mutually opposite.

3. The catheter device according to claim 1, wherein a three-layered structure is formed by slidably fitting an upper-layered tube onto a lower-layered tube of a main tube body with an outer tube slidably fit onto said upper-layered tube, and
   a stranding direction of said stainless steel wires of said outer tube and that of said upper-layered tube being mutually opposite, or
   a stranding direction of said stainless steel wires of said upper-layered tube and that of said lower-layered tube being mutually opposite.

4. The catheter device according to claim 1, wherein a three-layered structure is formed by slidably fitting an upper-layered tube onto a lower-layered tube of a main tube body with an outer tube slidably fit onto said upper-layered tube,
   a stranding direction of said stainless steel wires of said outer tube and that of said upper-layered tube being mutually opposite, and
   a stranding direction of said stainless steel wires of said upper-layered tube and that of said lower-layered tube being mutually opposite.

5. The catheter device according to claim 1, 2, 3 or 4, wherein an inner surface of said flexible hollow tube body is represented by a convex-concave structure to provide said helical grooves by said stainless steel wires, each formed semi-circular in cross section along a lengthwise direction of said flexible hollow tube body.

* * * * *